US006411760B1

United States Patent
Avellanet

(10) Patent No.: US 6,411,760 B1
(45) Date of Patent: Jun. 25, 2002

(54) MULTIFILAMENT TWISTED AND DRAWN TUBULAR ELEMENT AND CO-AXIAL CABLE INCLUDING THE SAME

(75) Inventor: Francisco J. Avellanet, Coral Gables, FL (US)

(73) Assignee: General Science & Technology Corp, Miami, FL (US)

(*) Notice: Subject to any disclaimer, the term of this patent is extended or adjusted under 35 U.S.C. 154(b) by 0 days.

(21) Appl. No.: 09/523,234

(22) Filed: Mar. 10, 2000

Related U.S. Application Data

(63) Continuation-in-part of application No. 09/290,774, filed on Apr. 13, 1999, now abandoned, and a continuation-in-part of application No. 09/484,819, filed on Jan. 18, 2000, now abandoned, which is a continuation-in-part of application No. 09/450,879, filed on Nov. 29, 1999, now Pat. No. 6,248,955, which is a continuation of application No. 08/843,405, filed on May 2, 1997, now Pat. No. 5,994,647.

(51) Int. Cl.$^7$ .................................................. G02B 6/44
(52) U.S. Cl. ........................ 385/104; 385/100; 385/101; 174/128.1
(58) Field of Search ................................. 385/100–114; 174/68.1, 70 R, 72 R, 108, 117 R, 128.1, 128.2, 125.1, 126.1, 113 R, 36, 109

(56) References Cited

U.S. PATENT DOCUMENTS

| 4,654,477 A | 3/1987 | Isoda .................... 174/128 R |
| 4,695,127 A | 9/1987 | Ohlhaber ................ 350/96.23 |
| 4,778,236 A | 10/1988 | Carroll ................... 350/96.23 |
| 4,861,947 A | 8/1989 | Altermatt et al. .......... 174/113 |
| 4,867,527 A | 9/1989 | Dotti ..................... 350/96.23 |
| 4,896,939 A | 1/1990 | O'Brien .................. 350/96.23 |
| 5,159,157 A | 10/1992 | Diegmann ................. 174/113 |
| 5,171,941 A | 12/1992 | Shimizu et al. ........... 174/125.1 |
| 5,198,621 A | 3/1993 | Kojima .................... 174/128.1 |
| 5,216,205 A | 6/1993 | Fujii ...................... 174/128.1 |
| 5,217,026 A | 6/1993 | Stoy et al. ................ 128/772 |
| 5,408,560 A | 4/1995 | Seynhaeve ................. 385/101 |
| 5,418,878 A | 5/1995 | Sass et al. ................ 385/101 |
| 5,467,420 A | 11/1995 | Rohrmann et al. ........... 385/101 |
| 5,469,523 A | 11/1995 | Blew et al. ............... 385/101 |
| 5,496,969 A | 3/1996 | Blackmore ................. 174/113 R |
| 5,523,528 A * | 6/1996 | Bese et al. ................ 174/36 |
| 5,555,338 A | 9/1996 | Haag et al. ............... 385/101 |
| 5,574,260 A | 11/1996 | Broomall et al. .......... 174/102 R |
| 5,574,815 A | 11/1996 | Kneeland ................. 385/101 |
| 5,602,953 A | 2/1997 | Delage et al. ............ 385/101 |
| 5,651,081 A | 7/1997 | Blew et al. ............... 385/101 |
| 5,666,453 A | 9/1997 | Dannenmann ............... 385/101 |
| 5,677,974 A | 10/1997 | Elms et al. .............. 385/101 |
| 5,687,271 A | 11/1997 | Rabinowitz ............... 385/101 |
| 5,745,627 A | 4/1998 | Arroyo et al. ............ 385/101 |

OTHER PUBLICATIONS

Net article entitled "Anixter announces Lucent Technologies' gigaspeed cabling solution as first available ALC 7 solution", Jun. 4, 1998., 4 pages.

* cited by examiner

Primary Examiner—Phan T. H. Palmer
(74) Attorney, Agent, or Firm—David P Gordon; David S Jacobson; Thomas A Gallagher

(57) ABSTRACT

A coaxial cable includes an inner conductor, a multifilament twisted and drawn or swaged tubular cable outer conductor, and a dielectric (insulative) material therebetween. According to one embodiment, the filaments of the multifilament twisted and drawn or swaged outer conductor are twisted about a central inner conductor provided with an insulative sheath. The outer conductor filaments are arranged such that when they are drawn or swaged, the compressive forces are directed on neighboring filaments and not directed radially inward toward the inner conductor, thereby preventing deformation of the inner conductor. According to another embodiment, each of the filaments is provided with an insulative sheath. According to other embodiments, a cable is formed with a central filament harder than the surrounding filaments. The central filament is withdrawn leaving behind a twisted and drawn or swaged tube with a hollow.

28 Claims, 4 Drawing Sheets

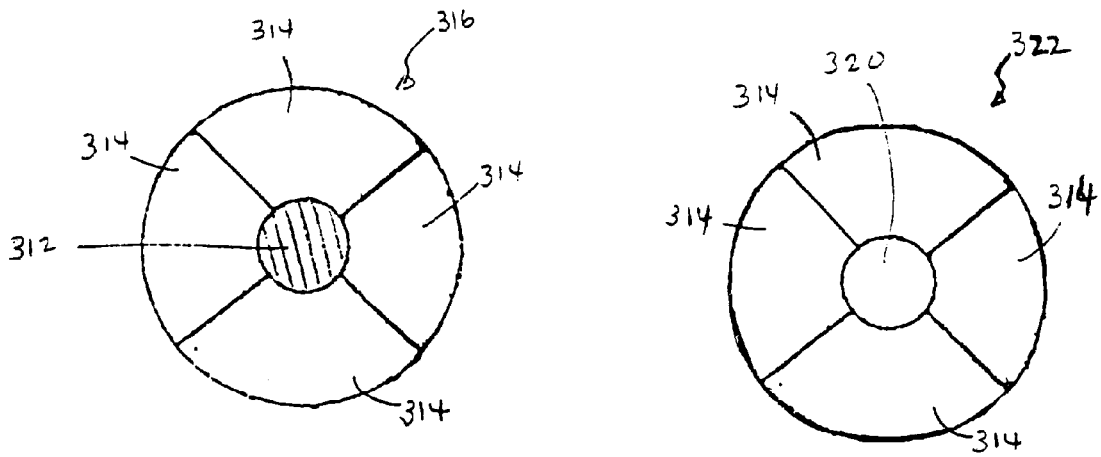
FIG. 9
FIG. 10
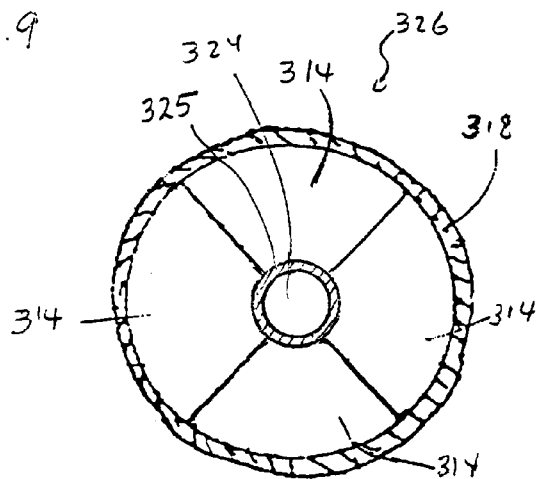
FIG. 11
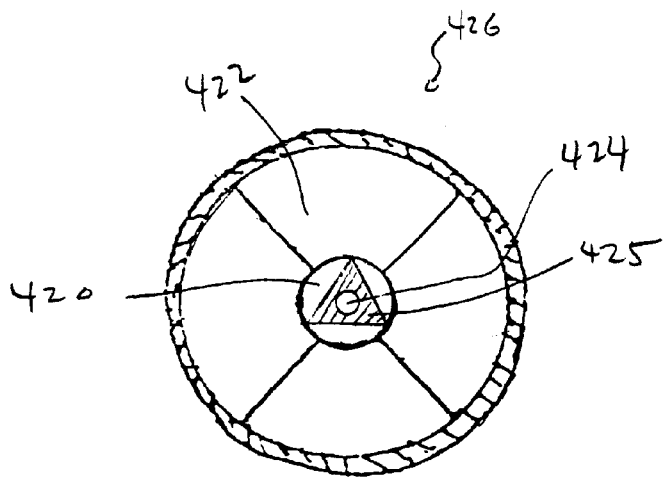
FIG. 12

MULTIFILAMENT TWISTED AND DRAWN TUBULAR ELEMENT AND CO-AXIAL CABLE INCLUDING THE SAME

This application is a continuation-in-part of U.S. Ser. No. 09/290,774, filed Apr. 13, 1999 now abandoment, and a continuation-in-part of U.S. Ser. No. 09/484,819, filed Jan. 18, 2000 now abandoment, each of which is hereby incorporated by reference herein in its entirety, which is a continuation-in-part of application Ser. No. 09/450,879, filed Nov. 29, 1999, which is a continuation of Ser. No. 08/843,405, filed May 2, 1997, now U.S. Pat. No. 5,994,647.

BACKGROUND OF THE INVENTION

1. Field of the Invention

This invention relates broadly to electrical cables. More particularly, this invention relates to coaxial cables including twisted and drawn or swaged elements.

2. State of the Art

Wire is manufactured from ingots using a rolling mill and a drawing bench. The preliminary treatment of the material to be manufactured into wire is done in the rolling mill where white hot billets (square section ingots) are rolled to round wire rod. The action of atmospheric oxygen causes a coating of mill scale to form on the hot surface of the rod which must be removed. This descaling can be done by various mechanical methods (e.g., shot-blasting) or by pickling, i.e., immersion of the wire rod in a bath of dilute sulfuric or hydrochloric acid. After pickling, the wire rod may additionally undergo a jolting treatment which dislodges the scale loosened by the acid. The remaining acid is removed by immersion of the wire rod in lime water.

The actual process of forming the wire is called drawing and is carried out on the metal in a cold state with a drawing bench. Prior art FIG. 1 shows a simple drawing bench 10. The wire 12 is pulled through a draw plate 14 which is provided with a number of holes, e.g. 16, of various diameters. These holes taper from the diameter of the wire 12 that enters the hole to the smaller diameter of the wire 12' that emerges from the hole. The thick wire rod 12 is coiled on a vertical spool 18 called a swift and is pulled through the die by a rotating drum 20 mounted on a vertical, shaft 22 which is driven by bevel gearing 24. The drum can be disconnected from the drive by means of a clutch 26. To pass a wire through a hole, the end of the wire is sharpened to a point and threaded through the hole. It is seized by a gripping device and rapidly pulled through the hole. This is assisted by lubrication of the wire. Each passage through a hole reduces the diameter of the wire by a certain amount. By successively passing the wire through holes of smaller and smaller diameter, thinner and thinner wire is obtained.

In the modern wire industry, instead of a draw plate, dies are used. Dies are precision-made tools, usually made of tungsten carbide for larger sizes or diamond for smaller sizes. The die design and fabrication is relatively complex and dies may be made of a variety of materials including single crystal natural or synthetic diamond, polycrystalline diamond or a mix of tungsten and cobalt powder mixed together and cold pressed into the carbide nib shape.

A cross section of a die is shown in prior art FIG. 2. Generally, the dies used for drawing wire have an outer steel casing 30 and an inner nib 32 which, as mentioned above, may be made of carbide or diamond or the like. The die has a large diameter entrance 34, known as the bell, which is shaped so that wire entering the die will draw lubricant with it. The shape of the bell causes the hydrostatic pressure to increase and promotes the flow of lubricant into the die. The region 36 of the die where the actual reduction in diameter occurs is called the approach angle. In the design of dies, the approach angle is an important parameter. The region 38 following the approach angle is called the bearing region. The bearing region does not cause diametric reduction, but does produce a frictional drag on the wire. The chief function of the bearing region 38 is to permit the conical approach surface 36 to be refinished (to remove surface damage due to die wear) without changing the die exit. The last region 40 of the die is called the back relief. The back relief allows the metal wire to expand slightly as the wire leaves the die. It also minimizes the possibility of abrasion taking place if the drawing stops or if the die is out of alignment with the path of the wire.

Although wire drawing appears to be a simple metalworking process, those skilled in the art will appreciate that many different parameters affect the physical quality of the drawn wire. Among these parameters, draw stress and flow stress play an important role. If these parameters are not carefully considered, the drawn wire may have reduced tensile strength. A discussion of the practical aspects of wire drawing can be found in Wright, Roger N., "Mechanical Analysis and Die Design", Wire Journal, October 1979, the complete disclosure of which is hereby incorporated by reference herein.

The wire forming processes described above may be used to form different kinds of wires including wires which are used to conduct electricity and wires which are used as structural supports. Generally, the most important physical characteristic of a wire used to conduct electricity is its electrical resistance. In all types of wires, flexibility may also be an important characteristic, with increased flexibility facilitating the snaking of wire through a tortuous path.

Cables are a bundle of wire strands held together, and typically include wire strands twisted together into a rope. Generally, a cable exhibits much more flexibility than a single wire of comparable diameter. Thus, in both structural and electrical applications, where flexibility is important, stranded cables are generally used rather than single solid wires. Stranded cables also have the advantage that they do not kink as easily as solid Wires and they can be connected to terminals by crimping. However, stranded cables have some disadvantages, including lower tensile strength and higher electrical resistance than solid wires of comparable diameter. In addition, the rough outer surface presented by stranded cables makes them more difficult to insulate than solid wires.

Prior art FIGS. 3 and 4 schematically illustrate an electrical transmission cable 50, in which several strands of wire are twined to produce a flexible cable having an overall diameter D, but which has a smaller cross sectional area than a solid wire with the same diameter. The cable 50 is shown consisting of seven wire strands 52, 54, 56, 58, 60, 62, 64 each having a diameter "d". In actual practice, an electrical transmission cable may consist of many more conductive strands and one or more steel core strands which serve to enhance the tensile strength of the cable. As shown, the seven strands are twined to form the conductive cable 50 having an overall diameter "D" which is approximately 2.15 d. However, the cross sectional area of the conductive cable 50, for purposes of computing the resistance (or conductance) of the cable is not as large as the cross sectional area of a solid wire having a diameter of 2.15 d. Thus, the stranded and twined cable 50 will have a higher resistance than a solid single strand of wire with the same cross sectional diameter.

Coaxial cable is another type of cable, and is suitable as a signal transmission medium. Coaxial cable generally consists of an unbalanced pair of conductors, in which an inner conductor is surrounded by an outer conductor (shielding layer), and the two conductors are held in a concentric relationship by a dielectric (insulator). The inner conductor is typically a single strand of drawn wire, while the outer conductor is typically a tubular braid of individually drawn wires or a conductive foil. The dielectric can be of many different types including polyethylene, polyvinyl chloride, gas injected foams (e.g., nitrogen gas-injected foam polyethylene), other foams, Spirafil®, and air or another gas. Where the dielectric is air or another gas, the inner conductor is maintained in position by the use of discrete spacers. For long-distance telecommunication signal transmissions, coaxial cables are provided in two standard gauges. Small gauge cable includes an inner conductor having an outer diameter of approximately 0.047 inches, and an outer conductor having an outer diameter of 0.174 inches. Large gauge cable has an inner conductor having an outer diameter of approximately 0.104 inches and an outer conductor having an outer diameter of approximately 0.375 inches. The use of a solid wire inner conductor having a diameter of 0.047 inches or 0.104 inches limits the flexibility of the standard coaxial cables. However, unlike electrical transmission lines, a stranded cable is typically not suitable for the central conductor due to standard connectors adapted for terminating free ends of the cable.

SUMMARY OF THE INVENTION

It is therefore an object of the invention to provide a coaxial cable which is highly flexible.

It is also an object of the invention to provide a coaxial cable which has a low electrical resistance.

It is a further object of the invention to provide coaxial cable which maximizes the combined cross-sectional areas of the electrical conductors.

In accord with these objects, which will be discussed in detail below, a coaxial cable includes an inner conductor, a multifilament twisted and drawn or swaged tubular cable outer conductor, and a dielectric (insulative) material therebetween. The coaxial cable preferably includes an outer insulative sheath.

According to a first embodiment of the invention, the filaments of the multifilament twisted and drawn or swaged outer conductor are twisted about an insulative sheath which surrounds a central inner conductor. The outer conductor filaments are arranged such that when they are drawn or swaged, the compressive forces are directed on neighboring filaments and not directed radially inward toward the inner conductor, thereby preventing deformation of the inner conductor.

According to a second embodiment of the invention, each of the filaments of the multifilament twisted and drawn or swaged outer conductor are provided with an insulative sheath and twisted about a central inner conductor. The outer conductor filaments are arranged such that when they are swaged, the compressive forces are directed on neighboring filaments and not directed radially inward toward the inner conductor, thereby preventing deformation of the inner conductor. After twisting and drawing, the insulative sheaths about the filaments form a dielectric layer between the inner and outer conductors.

According to third and fourth embodiments of the invention, a multifilament twisted and drawn or swaged cable is formed with a central filament harder than the surrounding filaments. The central filament is subsequently withdrawn from the surrounding filaments leaving behind a twisted and drawn or swaged tube with a central opening. An insulated conductor is then fed into or pulled through the central opening of the twisted and drawn or swaged tube to provide a coaxial cable. The insulation about the conductor may be circular in exterior cross-section, according to the third embodiment, or non-circular in exterior cross-section according to the fourth embodiment.

With the above embodiments, a coaxial cable is provided having increased flexibility relative to a wire, or standard coaxial cable of the same diameter. In addition, the multifilament twisted and drawn or swaged cable outer conductor has a smaller diameter than a twisted cable of the same cross-sectional area. Furthermore, the multifilament twisted and drawn or swaged conductor cable has a tensile strength greater than a wire or cable of the same diameter. As a result, coaxial cables constructed from the multifilament twisted and drawn or swaged conductor cable have greater flexibility and greater strength relative to other coaxial cables.

Additional objects and advantages of the invention will become apparent to those skilled in the art upon reference to the detailed description taken in conjunction with the provided figures.

BRIEF DESCRIPTION OF THE DRAWINGS

FIG. 9 is a cross sectional view of a coaxial cable according to a third embodiment of the invention prior to drawing through reducing dies or swaging;

FIG. 10 is a cross sectional view of a twisted and drawn or swaged tubular cable according to the third embodiment of the invention;

FIG. 11 is a cross sectional view of a coaxial cable according to the third embodiment of the invention; and FIG. 12 is a cross sectional view of a coaxial cable according to a fourth embodiment of the invention.

DETAILED DESCRIPTION OF THE PREFERRED EMBODIMENTS

Figure 1:
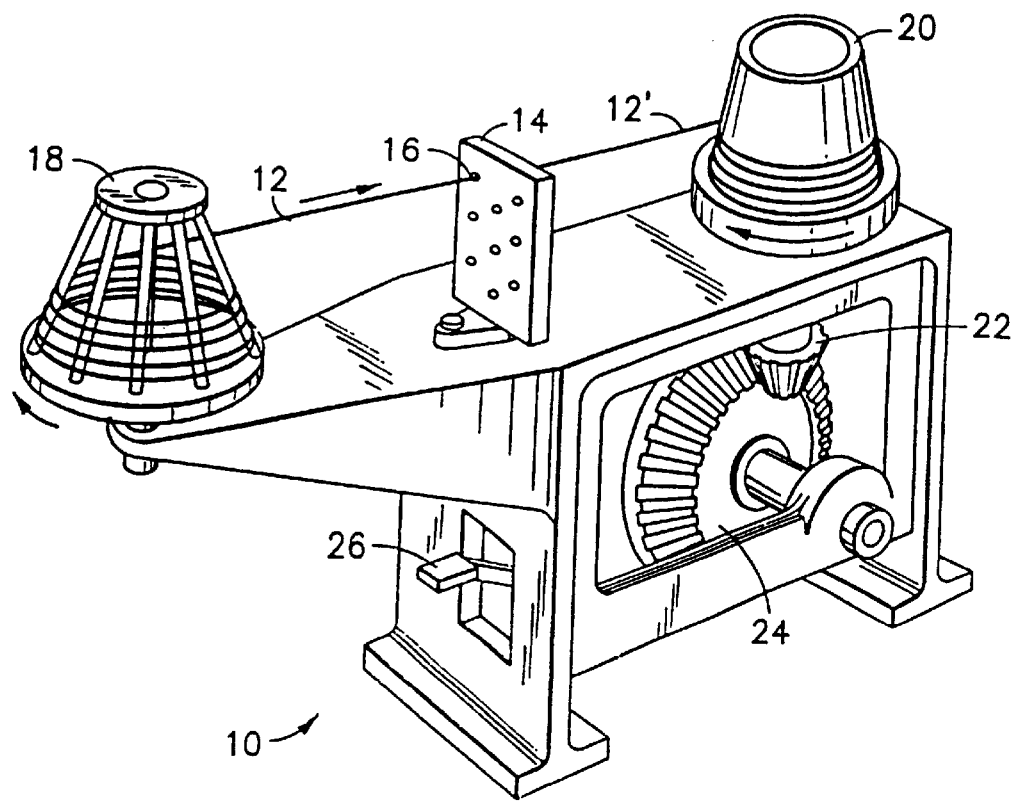
FIG. 1 is a schematic perspective view of a prior art wire drawing apparatus.
Figure 2:
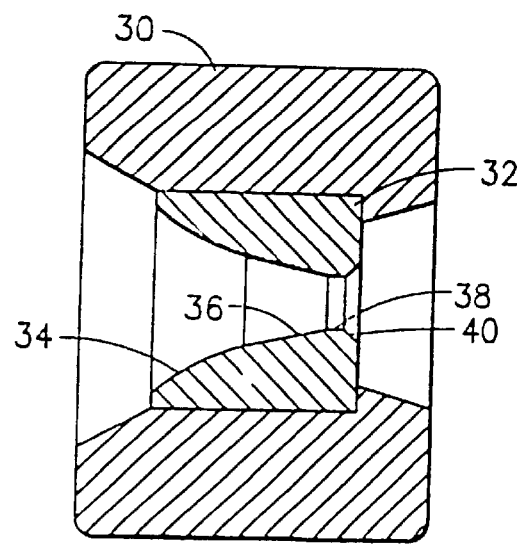
FIG. 2 is a schematic sectional view of a prior art drawing die.
Figure 3:
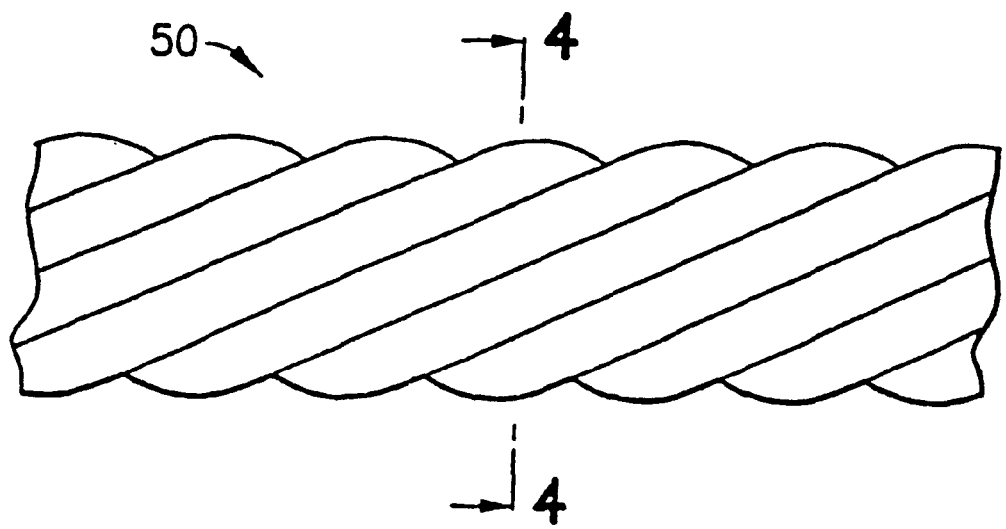
FIG. 3 is a broken schematic side elevation view of a prior art wire rope conductor.
Figure 4:
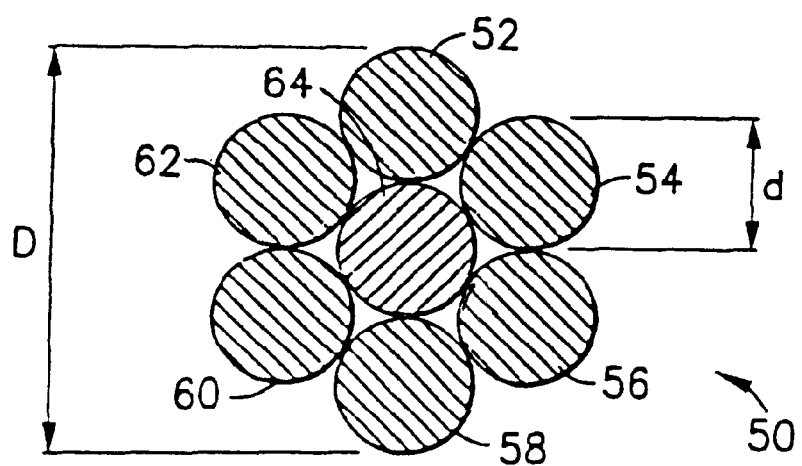
FIG. 4 is a cross-sectional view of the prior art wire rope conductor taken along line 4—4 in FIG. 3.
Figure 5:
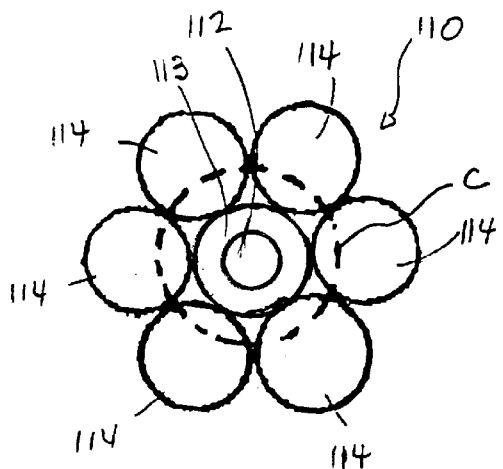
FIG. 5 is a cross sectional view of a coaxial cable assembly according to a first embodiment of the invention prior to drawing through reducing dies or swaging.

Turning now to FIG. 5, a compound multifilament rope 110 for a coaxial cable 116 (FIG. 6) according to a first embodiment the invention is shown. The compound multifilament rope 110 includes a central core conductor 112, which may be a single wire, a bundle of wires, or a multifilament twisted and drawn or swaged cable. In general, a multifilament twisted and drawn cable is manufactured by twisting a plurality of filaments into a wire rope and then pulling the wire rope through one or more successive dies using known wire drawing methods and apparatus whereby its diameter is decreased into the core conductor. The core conductor 112 is covered in an insulative material 113, such as an extruded or spray-coated layer of polyurethane, PTFE, or FEP. Six outer conductor wires 114 surround the central conductor 112. The central conductor 112 and outer wires 114 of the multifilament rope 110 are preferably being made from metal, e.g., copper, silver, gold, or aluminum, or a metal alloy, e.g., steel or nickel-titanium. If desired, the core conductor 112 and outer wires 114 may be wires made of a first metal and plated with another, typically softer metal.

Figure 6:
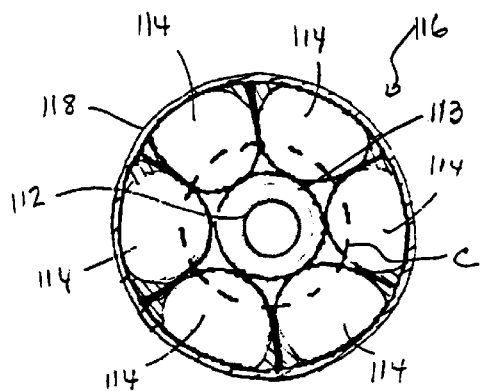
FIG. 6 is a cross sectional view of the coaxial cable of the first embodiment of the invention after drawing through reducing dies or swaging.

The outer wires 114 are twisted about the central conductor 112 to form the multifilament rope 110 with the outer wires 114 contacting each other along the dotted circle C illustrated in FIG. 5. The multifilament rope 110 is then pulled through a die using known wire drawing methods and apparatus whereby its diameter is decreased. Preferably, the multifilament rope 110 is successively drawn through dies of decreasing diameter. During the drawing process, the outer wires 114 are provided in a circle of equilibrium; that is, the inward compressive forces that develop during the drawing process are distributed fairly evenly onto the outer wires of the assembly which are held in this equilibrium arrangement by the presence of the central conductor 112 and the insulation 113 around the central conductor. As the central conductor 112 and insulation 113 serve to maintain the outer wires 114 in equilibrium, they are not subject to inward compressive forces and therefore are not distorted or crushed during the drawing process. Referring to FIG. 6, as a result, the outer wires 114, rather than moving inward, are plastically deformed, with the outer wire material yielding and flowing into the interstices (indicating by thatching) outside the circle of equilibrium C to form a first embodiment of the coaxial cable 116 of the invention. After the successive drawing is completed, the cable 116 assumes a substantially circular cross section.

According to a presently preferred embodiment, the multifilament rope is successively pulled through two or more dies of decreasing diameter. The resulting coaxial cable 116 has a diameter which is preferably approximately 25% smaller than the diameter of the multifilament rope 110. Alternatively, the multifilament rope 110 may be swaged to have a substantially circular cross-section and a reduced diameter. The construction of multifilament twisted and drawn or swaged cables is also described in detail in U.S. Ser. No. 08/843,405 now U.S. Pat. No. 5,994,647 and Ser. No. 08/856,571 now abandoned, which are hereby incorporated by reference herein in their entireties. The coaxial cable 116 exhibits relatively high flexibility and tensile strength relative to coaxial cables which do not utilize twisted and drawn or swaged constructs. In addition, the coaxial cable can be manufactured in a continuous process to produce cable of any length. A coaxial cable produced in this manner may have a natural curl, which may then be straightened (mechanically or otherwise), and preferably without a level of heat which could detrimentally affect the insulative material 113 about the central conductor 112. An insulative jacket or coating 118 is also preferably provided over the exterior of the cable 116.

Figure 7:
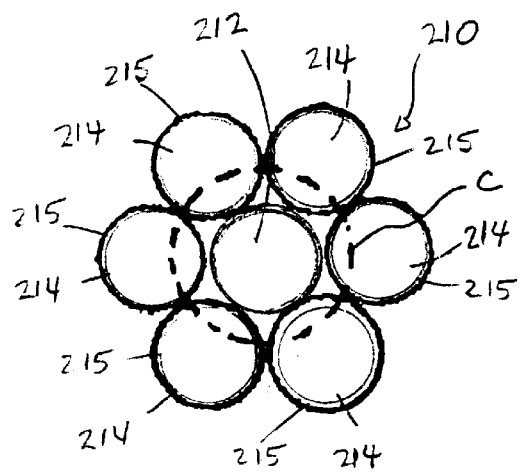
FIG. 7 is a cross sectional view of a coaxial cable assembly according to a second embodiment of the invention prior to swaging.

Turning now to FIG. 7, a second embodiment of a multifilament rope 210 is shown. The outer wires 214 of the multifilament rope 210 are each individually coated with an insulating material 215, and the inner conductor 212 is preferably bare. The outer wires 214 are twisted about the central conductor 212 to form the multifilament rope 210 with the insulating material 215 of each of the outer wires 114 contacting each other along the dotted circle C illustrated in FIG. 7.

Figure 8:
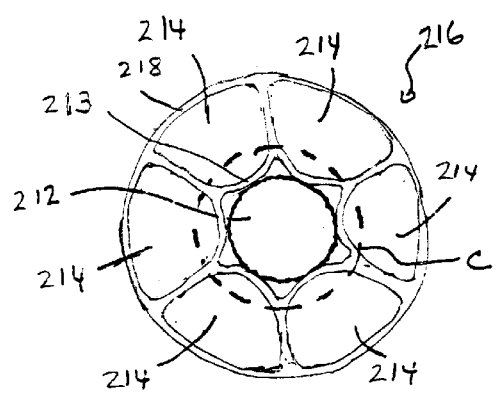
FIG. 8 is a cross sectional view of the coaxial cable of the second embodiment of the invention after swaging.

The multifilament rope 210 is then preferably swaged. During the swaging process, the outer wires 214 are provided in a circle of equilibrium. Referring to FIG. 8, therefore, the outer wires 214, rather than moving inward, are plastically deformed, with the outer wire material yielding and flowing into the interstices outside the circle of equilibrium C and the insulating material yielding to form a dielectric layer 213 between the inner conductor 212 and outer wires 214. The insulating material may also form an exterior insulating jacket 218 about the cable 216.

Referring now to FIGS. 9 through 11, a third embodiment of a coaxial cable 326 according to the invention is now described. Referring to FIG. 9, a twisted and drawn or swaged cable 316 is manufactured having a relatively hard central wire mandrel 312 typically having low conductivity, e.g., stainless steel, and four relatively softer conductive metal outer wires 314, e.g., copper. The twisted and drawn or swaged cable 316 is manufactured substantially as described above, i.e., by twisting the outer wires about the central wire to form a multifilament rope and then drawing the rope through one or more dies or swaging the rope to form a cable of reduced diameter. Referring to FIGS. 9 and 10, after drawing or swaging, the central wire mandrel 312 is pulled, to withdraw the central wire from the center 320 of the cable, thereby providing a twisted and drawn or swaged tubular cable 322; i.e., a cable having a central opening. If desired, in order to expedite removal of the central wire, the central wire and the outer wires may be subjected to differential temperatures. Referring to FIG. 11, a central core conductor 224 (having conductivity greater than the wire mandrel 312) and having an insulative coating 325 thereabout is then thread or pulled through the central hole 320, e.g., by coupling the core conductor 324 to a trailing end of the pulled central wire mandrel 312 when the central wire mandrel is removed from the cable. If desired, the core conductor 224 may itself be a twisted and drawn or swaged cable is generally described above and described in more detail in U.S. Pat. No. 5,994,647, and U.S. Ser. No. 08/963,686, now U.S. Pat. No. 6,049,042 and Ser. No. 09/484,819, which are hereby incorporated by reference herein in their entireties. The insulative coating 325 about the core conductor 324 preferably has a circular exterior cross-sectional shape, and the core conductor 324 and coating 325 together preferably have a diameter which substantially fills the central hole 320. The resulting coaxial cable 326 is then preferably provided with an insulative jacket or coating 318. The third embodiment of the coaxial cable is particularly useful for applications requiring relatively short discrete lengths of coaxial cable, e.g., under 100 meters.

Turning now to FIG. 12, a fourth embodiment of a coaxial cable 426, substantially similar to the third embodiment, is shown. The coaxial cable 426 is manufactured in substantially the same manner as the third embodiment. However, the core conductor 424 is provided with an insulative coating 425 having a triangular cross-sectional shape. The insulative coating 425 about the core conductor 424 may alternatively be provided with other non-circular cross-sectional shapes, e.g., polygonal, cross-shaped, etc. As such, when the core conductor 424 is pulled through the central hole 420, the exterior of the insulative coating 425 makes discrete point contact along the inner surface of the tubular cable 422 surrounding the central hole 420, thereby permitting easier pulling of the core conductor through the tubular cable. In addition, spaces are thereby provided longitudinally between the tubular cable 422 and the insulative coating 425, permitting the dissipation of heat which may otherwise cause attenuation of high frequency signals traveling along the coaxial cable 426. As with the coaxial cable of the third embodiment, if desired, the core conductor 424 of the fourth embodiment may be formed from a twisted and drawn or swaged cable.

It will be appreciated that each of the above embodiments provides a coaxial cable having increased flexibility and torqueability relative to coaxial cables which utilize a cable which has not been drawn or swaged. Furthermore, coaxial cables incorporating multifilament twisted and drawn or swaged cables have a tensile strength greater than coaxial cables which utilize a wire or cable of the same diameter. As a result, coaxial cables having multifilament twisted and drawn or swaged conductor cables have greater flexibility and greater strength relative to other coaxial cables.

There have been described and illustrated herein several embodiments of a coaxial cable and methods of making a coaxial cable. While particular embodiments of the invention have been described, it is not intended that the invention be limited thereto, as it is intended that the invention be as broad in scope as the art will allow and that the specification be read likewise. Thus, various aspects of the different embodiments of the invention may be mixed and matched to provide desired results. In addition, while a particular number of filaments have been described with respect to the manufacture of twisted and drawn or swaged cables for the coaxial cables, it will be appreciated that other numbers of filaments may be used. For example, there may be two or more outer filaments in the outer conductor of the coaxial cable. Also, while particular conductive materials have been described for the conductive filaments, it will be appreciated that other materials can be used as well. In addition, filaments of different materials may be combined into a single cable. Furthermore, filaments of nickel-titanium or other superelastic or shape memory alloys known in the art of shape memory alloys may be combined with filaments of more conductive materials. As such, the twisted and drawn or swaged cables may be constructed from a combination of materials to result in a cable have desired relative degrees of conductance, flexibility, and tensile strength, among other properties. Furthermore, all of the filaments comprising the outer "conductor" or all of the filaments comprising the inner or core "conductor", but not both, may be made from relatively low conductive superelastic or shape memory alloys, thereby, in effect, making a highly flexible single conductor cable. In addition, the methods provided here in may be used to create coaxial cables of various dimensions. Also, while a particular number of dies for pulling the respective multifilament rope therethrough has been disclosed with respect to particular embodiments, it will be appreciated that in each embodiment one or,more dies may be used. Furthermore, while a preferred drawing or swaging produces a 25% reduction in diameter, other reductions in diameter may be used. In addition, while particular insulative materials have been disclosed, other dielectric materials may also be used. It will therefore be appreciated by those skilled in the art that yet other modifications could be made to the provided invention without deviating from its spirit and scope as so claimed.

What is claimed is:

1. A coaxial cable, comprising:
   a) a plurality of filaments twisted and drawn together through at least one die or swaged to form a tubular outer conductor defining a longitudinal hollow space;
   b) a core conductor within said hollow space; and
   c) an insulative material dielectrically separating said core conductor from said outer conductor.

2. A coaxial cable according to claim 1, wherein:
   said insulative material is a coating on said core conductor.

3. A coaxial cable according to claim 1, wherein:
   said insulative material is a circumferential coating on each of said filaments of said outer conductor.

4. A coaxial cable according to claim 3, wherein:
   said insulative coating also forms an insulative jacket around said outer conductor.

5. A coaxial cable according to claim 1, wherein:
   said plurality of filaments of said outer conductor are comprised of at least one of copper, silver, gold, aluminum, steel, and a shape memory alloy.

6. A coaxial cable according to claim 1, wherein:
   said core conductor is a multifilament twisted and drawn or swaged cable.

7. A coaxial cable according to claim 1, wherein:
   said core conductor is a single core wire.

8. A coaxial cable according to claim 1, wherein:
   said core conductor is a bundle of wires.

9. A coaxial cable, comprising:
   a) a core conductor provided with an insulative material thereabout; and
   b) a plurality of metal or metal alloy filaments twisted and drawn together through at least one die or swaged coaxial with and external of said core conductor.

10. A coaxial cable according to claim 9, wherein:
    said core conductor is a multifilament twisted and drawn or swaged cable.

11. A coaxial cable according to claim 9, wherein:
    said core conductor is a single core wire.

12. A coaxial cable according to claim 9, wherein:
    said core conductor is a bundle of wires.

13. A coaxial cable according to claim 9, wherein:
    said insulative material has a non-circular exterior cross-sectional shape, and at least one space is provided between said insulative material and said metal or metal alloy filaments.

14. A method of making a coaxial cable, comprising:
    a) twisting a plurality of conductive strands about an insulated conductive core element to form a rope; and
    b) drawing the rope through at least one die to form a coaxial cable in which said conductive strands are dielectrically separated from said core element.

15. A method of making a coaxial cable, comprising:
    a) twisting a plurality of conductive strands about a conductive core element to form a rope, each of said conductive strands having an insulative material thereabout; and
    b) drawing the rope through at least one die or swaging the rope to form a coaxial cable in which said conductive strands are dielectrically separated from said core element.

16. A method of making a coaxial cable, comprising:
    a) providing a core element;
    b) arranging a plurality of metal or metal alloy filaments about said core element such that said filaments are in equilibrium, said filaments and core element together forming a rope; and
    c) drawing said rope through at least one die to form a cable, wherein at least one of said core element and said filaments are made of a conductive material.

17. A method according to claim 16, wherein:

said core element and at least one of said filaments are made of a conductive material, and said providing said core element includes providing said core element with an insulative coating thereabout.

18. A method according to claim 16, wherein:

said core element and at least one of said filaments are made of a conductive material, and said filaments made of said conductive material are provided with an insulative coating thereabout.

19. A method according to claim 16, further comprising:

d) straightening said coaxial cable.

20. A method according to claim 19, wherein:

said straightening is mechanically straightening.

21. A method of making a cable, comprising;

a) twisting a plurality of conductive strands about a central element to form a multifilament rope having a first diameter;

b) drawing the multifilament rope through at least one die or swaging the multifilament rope to form a cable having a reduced second diameter; and c) removing said central element from said cable to provide said cable with a longitudinal hollow.

22. A method according to claim 21, further comprising:

d) inserting a conductive element into said longitudinal hollow.

23. A method according to claim 22, wherein:

said conductive element includes an insulative material thereabout.

24. A method according to claim 23, wherein:

said insulative material has a non-circular cross-sectional shape.

25. A method according to claim 21, wherein:

said conductive element is a twisted and drawn or swaged cable.

26. A tubular cable made by the process of:

a) twisting a plurality of metal or metal alloy strands about a central element to form a multifilament rope having a first diameter;

b) drawing the multifilament rope through at least one die to form a cable having a reduced second diameter; and c) removing said central element from said cable to provide said cable with a longitudinal hollow.

27. A tubular cable according to claim 26, wherein:

said central element has a hardness greater than said metal or metal alloy strands.

28. A tubular cable according to claim 26, wherein:

said metal or metal alloy strands are made from at least one of copper, silver, gold, aluminum, steel, and a shape memory alloy.

* * * * *